US009554695B2

(12) United States Patent
Yamashita (10) Patent No.: US 9,554,695 B2
(45) Date of Patent: Jan. 31, 2017

(54) OPHTHALMOLOGIC INFORMATION PROCESS SYSTEM AND OPHTHALMOLOGIC APPLICATION

(71) Applicant: CANON KABUSHIKI KAISHA, Tokyo (JP)

(72) Inventor: Yutaka Yamashita, Shiroi (JP)

(73) Assignee: Canon Kabushiki Kaisha, Tokyo (JP)

( * ) Notice: Subject to any disclaimer, the term of this patent is extended or adjusted under 35 U.S.C. 154(b) by 416 days.

(21) Appl. No.: 14/068,181

(22) Filed: Oct. 31, 2013

(65) Prior Publication Data
US 2014/0132920 A1 May 15, 2014

(30) Foreign Application Priority Data
Nov. 9, 2012 (JP) ................................ 2012-247027

(51) Int. Cl.
| A61B 3/10 | (2006.01) |
| A61B 3/00 | (2006.01) |
| G06F 19/00 | (2011.01) |

(52) U.S. Cl.
CPC ........... *A61B 3/0025* (2013.01); *A61B 3/0016* (2013.01); *A61B 3/0033* (2013.01); *A61B 3/0058* (2013.01); *G06F 19/321* (2013.01)

(58) Field of Classification Search
CPC ....... A61B 3/00; A61B 3/0016; A61B 3/0033; A61B 3/0041; A61B 3/005; A61B 3/0058; A61B 3/14; A61B 3/145
USPC ......................................... 351/205, 206, 246
See application file for complete search history.

(56) References Cited

U.S. PATENT DOCUMENTS

| 6,659,610 B2 | 12/2003 | Kasahara | |
| 7,959,288 B2 | 6/2011 | Kogawa et al. | |
| 8,556,424 B2 * | 10/2013 | Iwase .................. | A61B 3/0025 351/205 |
| 8,801,179 B2 * | 8/2014 | Kishida ................ | A61B 3/1241 351/206 |

(Continued)

FOREIGN PATENT DOCUMENTS

| JP | 09-313438 A | 12/1997 |
| JP | 10-113334 A | 5/1998 |

(Continued)

OTHER PUBLICATIONS

Jun. 24, 2015 Chinese Official Action in Chinese Patent Appln. No. 201310549548.7.

*Primary Examiner* — Huy K Mai
(74) *Attorney, Agent, or Firm* — Fitzpatrick, Cella, Harper & Scinto (57) ABSTRACT

Selection items which can be executed by an ophthalmologic application are displayed on a display portion on an ophthalmologic apparatus, and can be selected and executed by an operation portion on the ophthalmologic apparatus, thereby providing an ophthalmologic information process system and program which can reduce load on the operator and increase the overall throughput of examination. An ophthalmologic application transmits executable selection item information to the ophthalmologic apparatus and causes the ophthalmologic apparatus to display the information. Selection of one of the displayed selection items is executed by operation on the ophthalmologic apparatus. The behavior of the application is then controlled in accordance with the selection item.

15 Claims, 9 Drawing Sheets

(56) References Cited

U.S. PATENT DOCUMENTS

| | | |
|---|---|---|
| 2002/0018179 A1 | 2/2002 | Hayashi et al. |
| 2002/0113942 A1 | 8/2002 | Kasahara |
| 2006/0025670 A1* | 2/2006 | Kim .................. A61B 3/00 |
| | | 600/407 |
| 2008/0030684 A1 | 2/2008 | Nawata et al. |
| 2009/0323023 A1 | 12/2009 | Kogawa et al. |
| 2012/0237108 A1 | 9/2012 | Yamashita |

FOREIGN PATENT DOCUMENTS

| | | |
|---|---|---|
| JP | 2002-191560 A | 7/2002 |
| JP | 2005-021206 A | 1/2005 |
| JP | 2006-280477 A | 10/2006 |
| JP | 2007-094471 A | 4/2007 |
| JP | 2007-319403 A | 12/2007 |
| JP | 2009-045218 A | 3/2009 |
| JP | 2009-106532 A | 5/2009 |
| JP | 2009-172157 A | 8/2009 |

* cited by examiner

OPHTHALMOLOGIC INFORMATION PROCESS SYSTEM AND OPHTHALMOLOGIC APPLICATION

BACKGROUND OF THE INVENTION

Field of the Invention

The present invention relates to an ophthalmologic information process system and an ophthalmologic application.

Description of the Related Art

It has been possible to transfer the images photographed by an ophthalmologic apparatus to an image filing system (for example, a system which manages photographed images during examination by the ophthalmologic apparatus), store the images in a computer, database, or the like, display the stored photographed images, and use them for diagnosis. In addition, some ophthalmologic apparatus (Japanese Patent Application Laid-Open No. H10-113334) can change settings on the ophthalmologic apparatus by opening a menu screen on the display of the ophthalmologic apparatus in order to change settings on the ophthalmologic apparatus during examination. Furthermore, some image filing system automatically shifts to a screen for the registration of the next object at the end of an examination in order to improve the examination efficiency (Japanese Patent Laid-Open No. 2009-045218).

According to the related art, however, since there is no means for causing an ophthalmologic apparatus to execute the function of an image filing system by operating the apparatus, the operability is poor. For example, after the operator terminates photographing operation with the operation portion of the ophthalmologic apparatus, the operator terminates the examination with the operation portion of the image filing system.

Providing a dedicated switch on the ophthalmologic apparatus side to solve the above problem makes it necessary to widen the operation portion, resulting in inconvenience.

In addition, a dedicated switch provided on an ophthalmologic apparatus is an unnecessary switch for an image filing system having no corresponding function. This may degrade the operability.

Instead of providing a dedicated switch, it is conceivable to make an image filing system execute its function by displaying a menu screen or the like on the display of an ophthalmologic apparatus. It is, however, necessary to implement this operation in consideration of both a process on the ophthalmologic apparatus side and the image filing system function. With an increase in the types of ophthalmologic apparatuses and image filing systems, it is difficult to manage combinations.

SUMMARY OF THE INVENTION

The present invention solves the above problems and provides an ophthalmologic information process system which can improve operability by making an image filing system execute its function by simple operation of an ophthalmologic apparatus and can make image filing systems execute their functions easily on the ophthalmologic apparatus side even with any difference in function between the systems to be used and an ophthalmologic application suitable for the ophthalmologic information process system.

According to an aspect of the present invention, there is provided an ophthalmologic information process system comprising an ophthalmologic apparatus including a photographing portion configured to photograph an ophthalmologic image, an operation portion including a selection information display key which displays selection information, a selection moving key which moves a selection item, and an execution key which executes the selection item, and a display portion configured to display the ophthalmologic image and the selection information, and an ophthalmologic application connected to the ophthalmologic apparatus and configured to record the ophthalmologic image photographed by the ophthalmologic apparatus, the ophthalmologic application including a memory portion configured to store selection item information as information which enables to select a specific function of the ophthalmologic application with the selection item, an image generation portion for ophthalmologic apparatus display configured to generate the selection item information as a selection information image configured to be displayed on the ophthalmologic apparatus, a reception unit configured to receive information including operation information of the operation portion which is transmitted from the ophthalmologic apparatus, a transmission unit configured to transmit the selection information image generated by the image generation portion for ophthalmologic apparatus display to the ophthalmologic apparatus, and a behavior control unit configured to control a behavior of the application in accordance with operation information of the operation portion which is included in the information received by the reception unit.

In addition, according to another aspect of the present invention, there is provided an ophthalmologic application which is connected to an ophthalmologic information process system comprising an ophthalmologic apparatus including a photographing portion configured to photograph an ophthalmologic image, an operation portion including a selection information display key which displays selection information, a selection moving key which moves a selection item, and an execution key which executes the selection item, and a display portion configured to display the ophthalmologic image and the selection information, and records the ophthalmologic image photographed by the ophthalmologic apparatus, the application comprising a memory portion configured to store selection item information as information which enables to select a specific function of the ophthalmologic application with the selection item, an image generation portion for ophthalmologic apparatus display configured to generate the selection item information as a selection information image configured to be displayed on the ophthalmologic apparatus, a reception unit configured to receive information including operation information of the operation portion which is transmitted from the ophthalmologic apparatus, a transmission unit configured to transmit the selection information image generated by the image generation portion for ophthalmologic apparatus display to the ophthalmologic apparatus, and a behavior control unit configured to control a behavior of the application in accordance with operation information of the operation portion which is included in the information received by the reception unit.

According to the present invention, it is possible to improve operability by making an image filing system execute its function by simple operation of an ophthalmologic apparatus and make image filing systems execute their functions easily on the ophthalmologic apparatus side even with any difference in function between the systems to be used.

Further features of the present invention will become apparent from the following description of exemplary embodiments with reference to the attached drawings.

BRIEF DESCRIPTION OF THE DRAWINGS

FIGS. 5A and 5B are views showing an example of displaying on the display portion of the ophthalmologic apparatus of the ophthalmologic information process system, in which

FIGS. 7A and 7B are views showing an example of a photograph preview image on the ophthalmologic information process system, in which

FIG. 8 is comprised of FIGS. 8A and 8B showing an example of a flowchart showing the menu operation of the ophthalmologic information process system.

DESCRIPTION OF THE EMBODIMENTS

Preferred embodiments of the present invention will now be described in detail in accordance with the accompanying drawings.

First Embodiment

Figure 1:
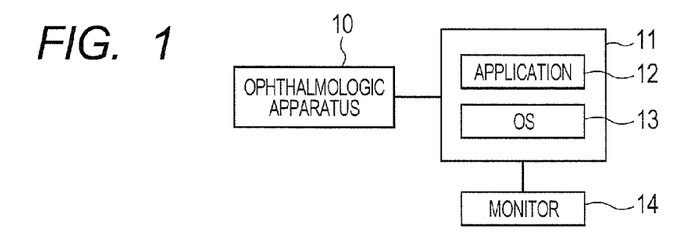
FIG. 1 is a block diagram showing an example of connection in an ophthalmologic information process system.

FIG. 1 shows the arrangement of an ophthalmologic information process system according to the first embodiment. The ophthalmologic information process system is provided with an ophthalmologic apparatus 10, a computer 11, an OS 13, and a monitor 14. The computer 11 executes an application 12 capable of performing image filing to record the ophthalmologic image photographed by the ophthalmologic apparatus.

The computer 11 may be connected to a database which archives and manages ophthalmologic images, patient information, and the like via a communication line such as a LAN (Local Area Network). For example, ophthalmologic photographing apparatuses include a fundus camera, an OCT (Optical Coherence Tomography), and an SLO (Scanning Laser Ophthalmoscope).

Figure 2:
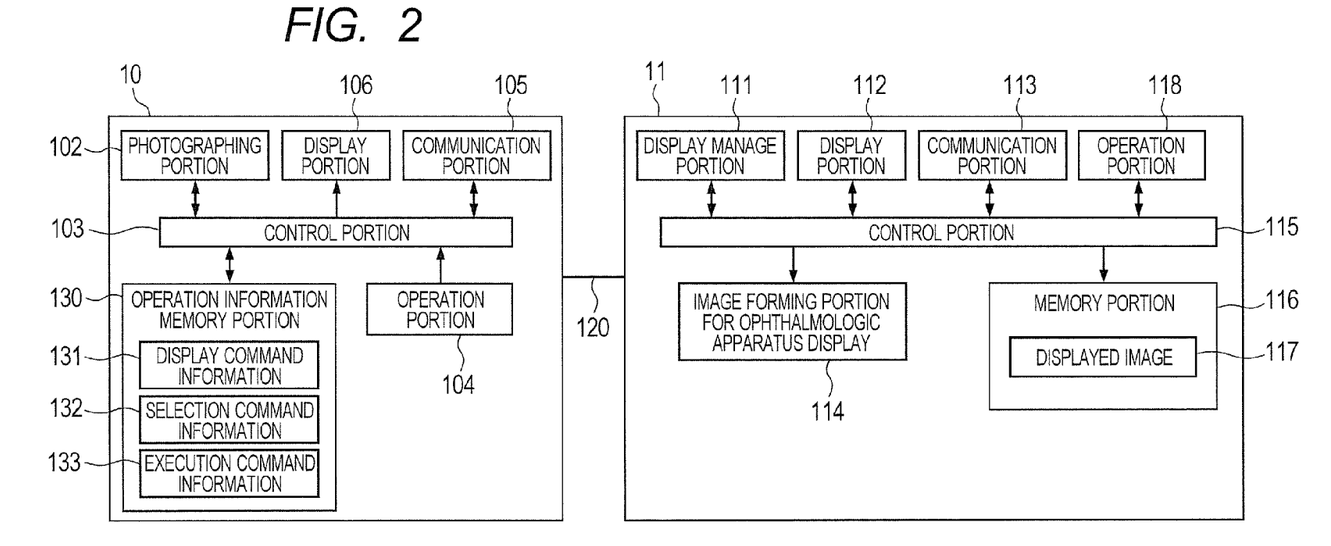
FIG. 2 is a block diagram showing the functional arrangement of the ophthalmologic information process system.

FIG. 2 is a block diagram showing the functional arrangement of the ophthalmologic apparatus 10 and application 12 constituting the ophthalmologic information process system shown in FIG. 1. As shown in FIG. 2, the ophthalmologic apparatus 10 is provided with a photographing portion 102, a control portion 103, an operation portion 104, a communication portion 105, a display portion 106, and an operation information memory portion 130 which stores operation information. The application 12 is provided with a display manage portion 111, a display portion 112, a communication portion 113, an image forming portion 114 for ophthalmologic apparatus display, a control portion 115, a memory portion 116 which stores a display image 117, and an operation portion 118. Note that the ophthalmologic apparatus 10 is connected to the application 12 via a communication line 120. The communication line 120 includes, for example, a USB (Universal Serial Bus) and WiFi as a wireless communication line.

The ophthalmologic apparatus 10 will be described first. Note that this embodiment uses a fundus camera as the ophthalmologic apparatus 10. The operation portion 104 includes a photograph switch and photographing operation portions such as a joystick for photograph mode switching, photographing region designation, observation light intensity or photographing light intensity adjustment, and alignment. Note that the operation portion 104 may not be a dedicated switch and may include arbitrary operation devices and input devices such as a keyboard, mouse, trackball, and touch panel.

The photographing portion 102 acquires a photographed ophthalmologic image. For example, ophthalmologic images include a fundus image photographed by the fundus camera, a tomographic image of the fundus photographed by the OCT, and an image of the retina or choroid photographed by the SLO. Note that the ophthalmologic apparatus 10 may be provided with a memory portion to store ophthalmologic images in association with photographing regions as photographing information, photographing times, and the like.

Figure 3:
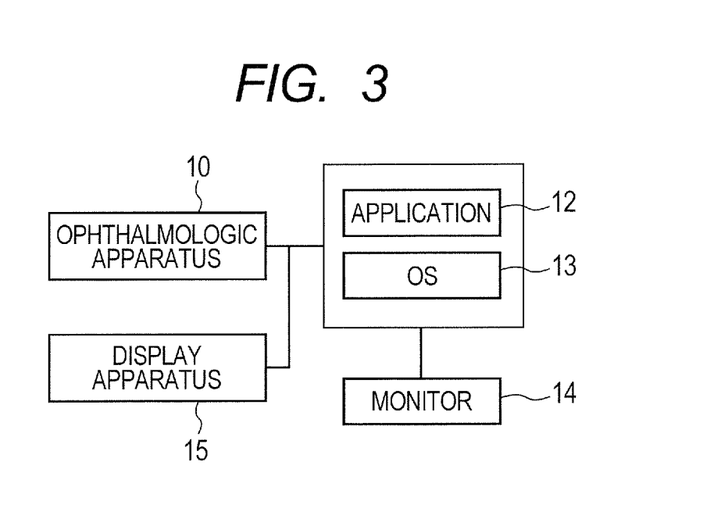
FIG. 3 is a block diagram, showing an example of connection in an arrangement in which the display apparatus of the ophthalmologic information process system is a discrete apparatus.

When the operator depresses the photograph switch of the operation portion 104, the apparatus displays the ophthalmologic image obtained by the photographing portion 102 on the display portion 106 via the control portion 103. The display portion is implemented by an arbitrary display such as an LCD (Liquid Crystal Display) or CRT (Cathode Ray Tube) display. Note that it is possible to use a device obtained by integrating an operation portion like a touch panel described in relation to the operation portion 104 and a display portion. In this case, the operation portion 104 and the display portion 106 shown in FIG. 2 are integrated. For example, as shown in FIG. 3, a display apparatus 15 is independently provided.

The communication portion 105 communicates with the application 12 via the communication line 120. The ophthalmologic apparatus 10 transmits an ophthalmologic image, photographing information, apparatus state, and operation information to the application 12 by this communication. Operation information includes display command information 131, selection command information 132, and execution command information 133. The operation information stored in the operation information memory portion 130 is one type of communication information for the communication of the content of operation of the operation portion 104 to the application 12. Note that the operation information memory portion 130 functions as a memory portion which stores selection item information as information which enables to select a specific function of the application 12 as an ophthalmologic application via a selection item in the present invention.

The communication portion 105 receives transmission information transmitted from the application 12. One type of such transmission information is a display image. Upon receiving a display image, the communication portion 105 displays the display image on the display portion 106.

The control portion 103 controls each portion of the ophthalmologic apparatus 10.

The application 12 will be described next. The application 12 has the memory portion 116 which archives and manages patient information and the like. The computer 11 acquires the ophthalmologic image photographed by the ophthalmologic apparatus 10 via the communication portion 113 and stores the image in the memory portion 116 in association with patient information and the like. The communication portion 113 has functions as a reception unit which receives information including operation information transmitted from the ophthalmologic apparatus 10 to the operation portion 104 and a transmission unit which transmits the selection information image generated by the image forming portion 114 to the ophthalmologic apparatus 10.

The acquired ophthalmologic image is displayed on the display portion 112 via the control portion 115. In addition, an ophthalmologic image, patient information, and the like are acquired by the communication portion 113 or by control portion 115 via a communication line such as a LAN or by connecting to a server which archives and manages ophthalmologic images, patient information, and the like. These pieces of information may be stored as information necessary for diagnosis in the memory portion 116.

The operation portion 118 includes arbitrary operation devices and input devices such as a keyboard, mouse, trackball, and touch panel. The operator inputs patient information and the like necessary for examination with the operation portion 118. The operator also selects an examination start to start an examination or an examination termination to terminate an examination with the operation portion 118.

When receiving the operation information stored in the operation information memory portion 130 upon operation of the ophthalmologic apparatus 10 via the communication portion 113, the control portion 115 operates the display manage portion 111. The display manage portion 111 reads an image and a display position from the display image 117 stored in the memory portion 116 in accordance with the received operation information. The image forming portion 114 then generates a display image. The generated display image is transmitted to the ophthalmologic apparatus 10 via the communication portion 113 and displayed on the display portion 106 of the ophthalmologic apparatus 10.

Figure 4:
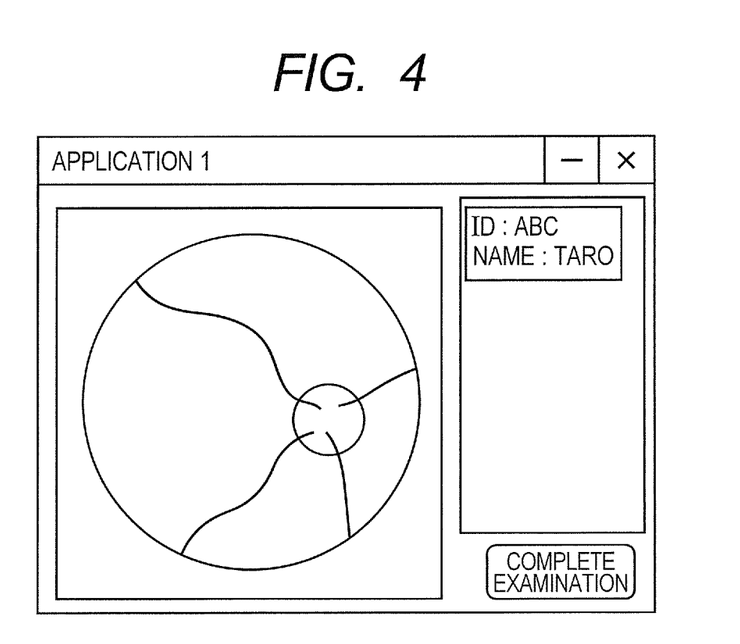
FIG. 4 is a view for explaining an ophthalmologic application for the ophthalmologic information process system.

FIG. 4 shows an example for explaining an ophthalmologic application as an application in the ophthalmologic information process system according to this embodiment. FIG. 4 shows an examination screen on the application. The application displays patient information and a photographed image. An examination termination button indicating the termination of examination is displayed on the screen on the application. When operator executes examination termination, the application stores patient information, examination information, and a photographed image in association with each other and closes the examination screen. When the operator executes examination starting operation, the application, opens the examination screen again.

Figure 5A:
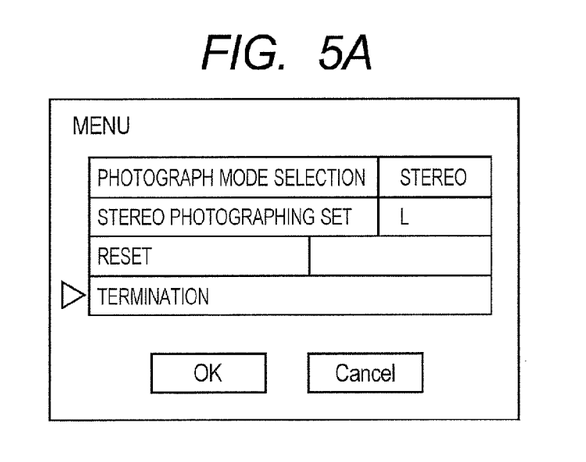
FIG. 5A shows an example of a menu screen on which examination termination is selected and FIG. 5B shows a screen example displaying the examination termination message displayed after examination termination is selected and executed in FIG. 5A.
Figure 5B:
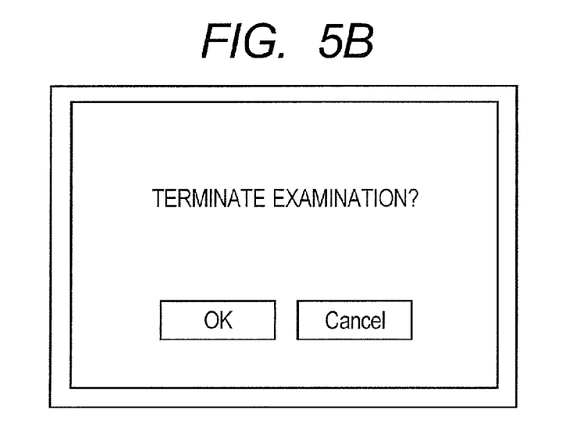

FIG. 5A shows a menu screen displayed on the display portion 105 of the ophthalmologic apparatus 10 in this embodiment. The display portion 106 generally displays an observation image of the anterior ocular segment or fundus but displays this menu screen when the operator performs menu display operation on the operation portion. For menu display, a dedicated switch may be provided on the ophthalmologic apparatus side. FIG. 5A shows a menu item for examination termination. When the operator selects and executes the examination termination with the operation portion 118, the application displays a confirmation screen for executing examination termination like that shown in FIG. 5B. When the operator selects the OK button, the application executes examination termination.

When the operator selects fundus image photographing operation or examination termination concerning the eye to be inspected on the menu screen, the application may execute examination termination without displaying any confirmation screen for examination termination upon executing the selected operation.

Figure 6:
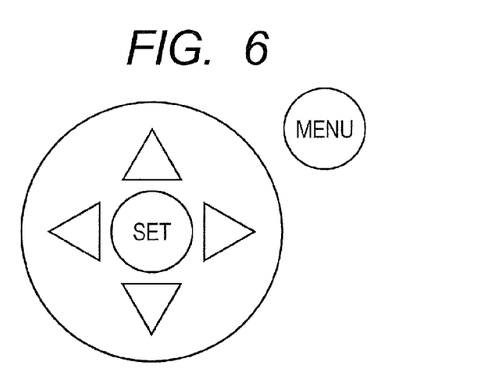
FIG. 6 is a view showing an example of an internal fixation target operation key and the menu display key on the operation portion of the ophthalmologic apparatus.

FIG. 6 shows an example of internal fixation target operation key and menu key. The internal fixation target operation key includes keys for moving the turn-on position vertically and horizontally and a key (SET) for highlighting the internal fixation target position. The menu key (MENU) is a key to be depressed to open the menu screen. In this embodiment, this operation key is assigned as a selection moving key for moving a selection item for election information, and the key for highlighting is assigned as an execution key for prompting the execution of a selected selection item. In consideration of the space on the apparatus, given keys may be integrated into one key. For example, the menu key may be omitted and the SET key may be assigned as a menu display key when the application disables the operation of highlighting the internal fixation target position.

Figures 8, 8A:
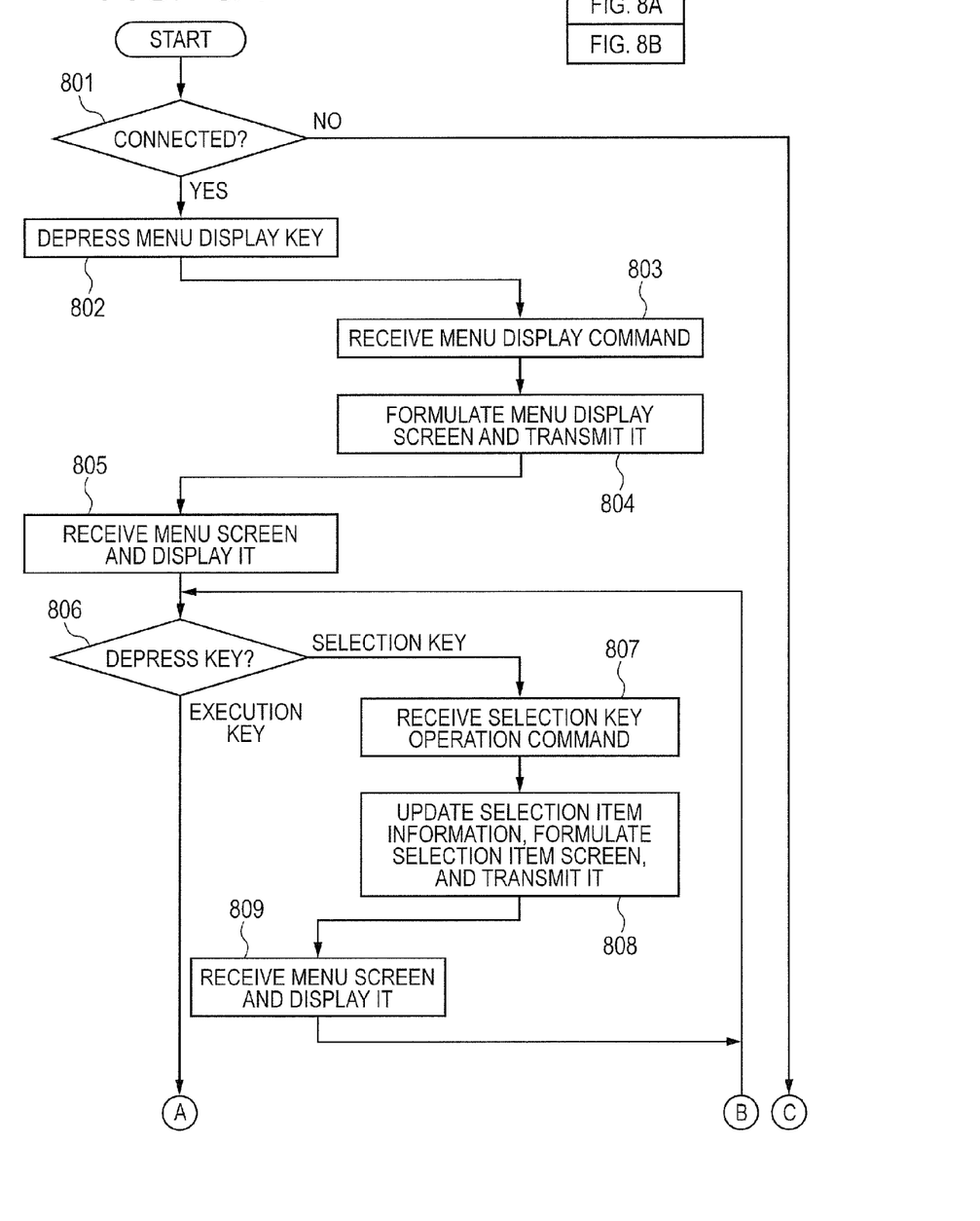

FIGS. 8A and 8E show a flowchart for operation on the menu screen in this embodiment. This flowchart will be described below with reference to FIGS. 4, 5A and 5B by exemplifying a fundus camera as a photographing apparatus of the embodiment, the internal fixation target operation keys provided on the fundus camera as the operation portion 104, and the menu image as the display image 117.

This system checks whether the fundus camera is connected to the application and they can communicate with each other (step 801). If they are not connected to each other, the system terminates the processing. Note that displaying a connection state on the display portion will make it more intelligible. For example, the system displays, on the display portion, information indicating that they are not connected or are connected. Although not shown in FIGS. 8A and 8B, the system terminates the processing when the connection is lost even in the processing after step 802.

In step 802, when the operator depresses the menu display key (not shown) provided on the fundus camera, the fundus camera detects that the menu display key is depressed. The menu display key corresponds to a selection information display key in the present invention. The system notifies the application that the operator has depressed the menu display key. In this embodiment, a state in which the menu display key is depressed corresponds to an anterior ocular segment alignment state.

In step 803, the application receives a menu display command as communication information from the fundus camera.

In step 804, the display manage portion 111 reads a menu screen from the memory portion 116. The display manage portion 111 also acguires the selection command information 132 and causes the image forming portion 114 to generate a menu image indicating a selected position as a selection information image which can be displayed on the ophthalmologic apparatus 10. The selected position at the time of opening the menu screen may be returned to the initial position every time the operator opens the menu or may be the position at the time of closing the previous menu. The display manage portion 111 transmits the image of the generated menu screen to the fundus camera.

In step 805, upon receiving the menu image, the fundus camera displays it as selection information on the display portion 106.

In step 806, the operator selects an item, to be executed by using the selection key while seeing the menu image. When the operator depresses the selection key, the fundus camera transmits selection key information to the application. The selection key corresponds to a selection moving key which moves a selection item in displayed selection information in the present invention.

Figure 8B:
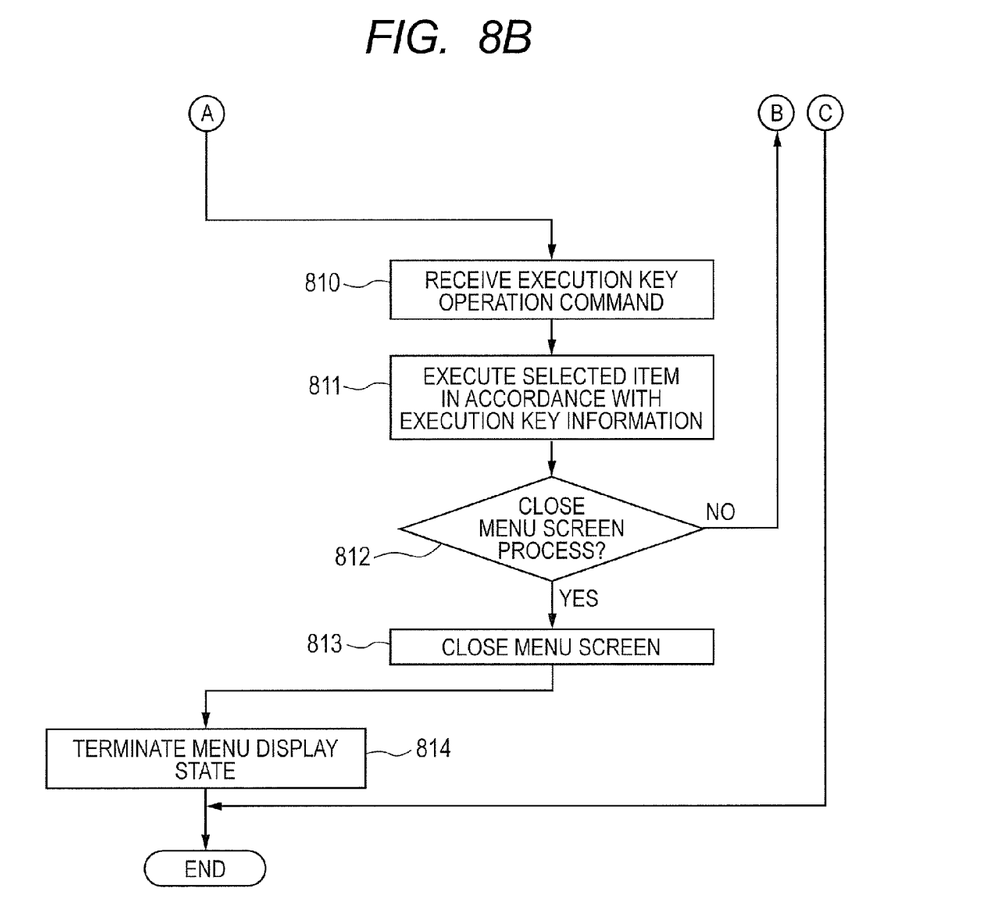

In step 807, the application 12 receives the selected key. In step 808, the application 12 updates the information of selection items and generates an image of a menu screen based on the updated selection items. The display manage portion 111 updates the selected states of selection items as selection item information. The generated image is transmitted to the fundus camera. In step 809, the fundus camera receives the menu screen and displays the received image. Subsequently, the process returns to step 806 to wait for selection key operation or execution key operation. Note that the execution key functions as an execution key which issues a command for executing the information selected by a selection item in the present invention. The above selection moving key and execution key are included in the operation portion for executing each operation mode of the ophthalmologic apparatus in the present invention.

A process of selecting examination termination will be described below. The operator vertically moves a menu item by using the up and down keys of the internal fixation target in FIG. 6. If the initial display position is at the photograph mode selection, operating the down key three times will select the examination termination as shown in FIG. 5A.

In step 806, when the operator operates the SET key assigned as the execution key shown in FIG. 6, the fundus camera transmits execution key information to the application 12.

In step 810, the application 12 receives execution key information. In step 811, the application 12 performs an execution process for the selection item based on the selection item information. The execution process for the selected item is executed by the control portion 115 functioning as an operation control unit which controls the behavior of the application 12 in accordance with the operation information of the operation unit on the ophthalmologic apparatus 10 side, which is included in the information received, by the application 12 in the present invention. If, for example, the operator selects examination termination, the application 12 generates an image of the confirmation screen for examination termination and transmits it to the fundus camera. The fundus camera receives the display image and displays the confirmation screen in FIG. 5B for examination termination.

In step 812, the system determines whether to perform a process for closing the menu screen. When continuing to display a menu screen, the operator selects "NO" in the process for the confirmation screen for examination termination. The process then returns to step 806. In the processing in step 806 to 809, the operator selects "OK" on the display screen. When the operator depresses the execution key while "OK" is selected, the application 12 executes a process for examination termination selected and displayed in the process in step 811. In this case, the application 12 executes the process for examination termination when the operator depresses the examination termination button shown in FIG. 4.

Since the process for examination termination is the process of closing the menu screen, the application 12 selects "YES" in step 812. In step 813, the application 12 performs the process of closing the menu screen. In the process of closing the menu screen, the application 12 generates an imago for displaying a display image, with the menu display key being depressed, at the time of alignment for anterior ocular segment observation, and transmits the image to the fundus camera. Upon receiving the image, the fundus camera displays the image to be displayed at the time of alignment for anterior ocular segment observation and terminates the process. Note that while the menu is displayed, the system may inhibit operations other than operations on the selection and execution keys, for example, operation on the photograph switch and changes in photograph mode.

As described in the first embodiment, according to the present invention, it is possible to execute a process on the application side by performing only operation on the fundus camera side. It is possible to perform comfortable operation without operating the mouse or the like on the application side.

Note that the ophthalmologic apparatus 10 may include a left/right eye detection unit which detects whether an eye to be inspected is the left or right eye and a left/right switching detection unit which detects that the left and right eyes to be photographed have been switched. In this case, while a selection information image is displayed on the display portion 106, when the left/right switching detection unit detects that the left and right eyes to be inspected have been switched, the control portion 115 may terminate the display of a selection information image on the display portion 106 and restore the initial display.

In addition, the ophthalmologic apparatus 11 may be provided with a photographing inhibition unit which temporarily inhibits photographing of an eye to be inspected. In this case, when the operator operates the selection information display key and a selection information image is displayed on the display portion 106, the photographing inhibition unit preferably inhibits photographing in accordance with a command from the control portion 115.

Second Embodiment

The second embodiment will exemplify a case in which a preview image is displayed as a confirmation image of a photographed image on an ophthalmologic apparatus and an application. The following is an example of displaying a preview image on the application side. A preview image is often displayed on one side under normal conditions, but it is sometimes preferable to display such images on two sides in the following cases.

The first is a case in which the display portion on the ophthalmologic apparatus is small, and the monitor as the display portion of an application is large. It is conceivable to use a large monitor on the application side to check an image in more detail.

The second is a case in which preview images are displayed at different timings. This operation is performed to allow the operator to quickly check a failed image due to the influences of the blinking of the eye and the like. Since the operator can check on a small screen, a preview image is displayed on the ophthalmologic apparatus side.

The third is a case in which different image process functions are provided on the two sides. If a function of performing an image process optimal for diagnosis is provided on the application side, the operator may check the image process result displayed as a preview image. Note that an image process includes the processing of improving the visualization of a lesion, blood vessel, or the like by adjusting luminance, contrast, and RGB and the processing of emphasizing the blood vessels.

Figure 7A:
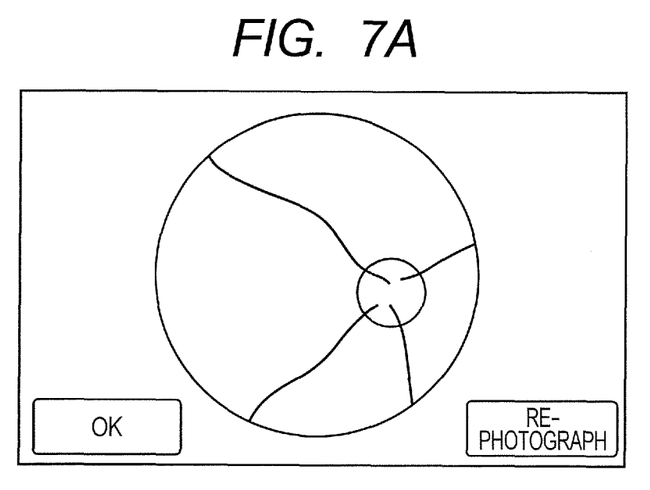
FIG. 7A shows an example of the preview screen displayed on the display portion of the ophthalmologic apparatus and FIG. 7B shows an example of the preview screen displayed on an ophthalmologic application.
Figure 7B:
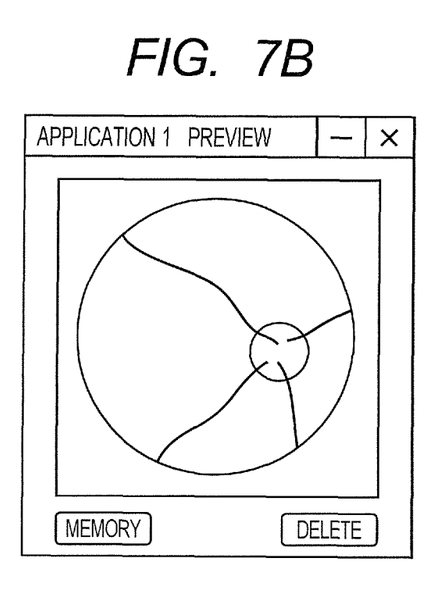

The fourth is a case in which the operator can select different functions on preview screens. FIGS. 7A and 7B show an example. The operator can select the processing of performing re-photographing on the preview on the ophthalmologic apparatus but cannot select it on the application side. In addition, although the operator can select, on the application side, whether to store or delete a photographed image, he/she cannot select the function on the ophthalmologic apparatus side. Assume that a preview image of a photographed image is displayed on the ophthalmologic apparatus and the image having undergone an image process is displayed on the preview screen on the application. In this case, in order to store the image and start the next photographing operation, the operator selects "OK" on the ophthalmologic apparatus side and then selects "memory" by operation on the application side, resulting in cumbersome operation.

In order to avoid, this cumbersome operation, the second embodiment will exemplify a case in which the system synchronously handles operations on two preview screens. In this case, when the operator selects "OK" on the preview screen on the ophthalmologic apparatus side, the system selects "memory" on the preview screen on the application side. The following will also describe the processing of selecting "delete" on the preview screen on the application side when the operator selects "re-photograph" on the preview screen on the ophthalmologic apparatus side.

The arrangement of the second embodiment is the same as that of the first embodiment. A display image 117 will be described as a preview image.

Figure 9:
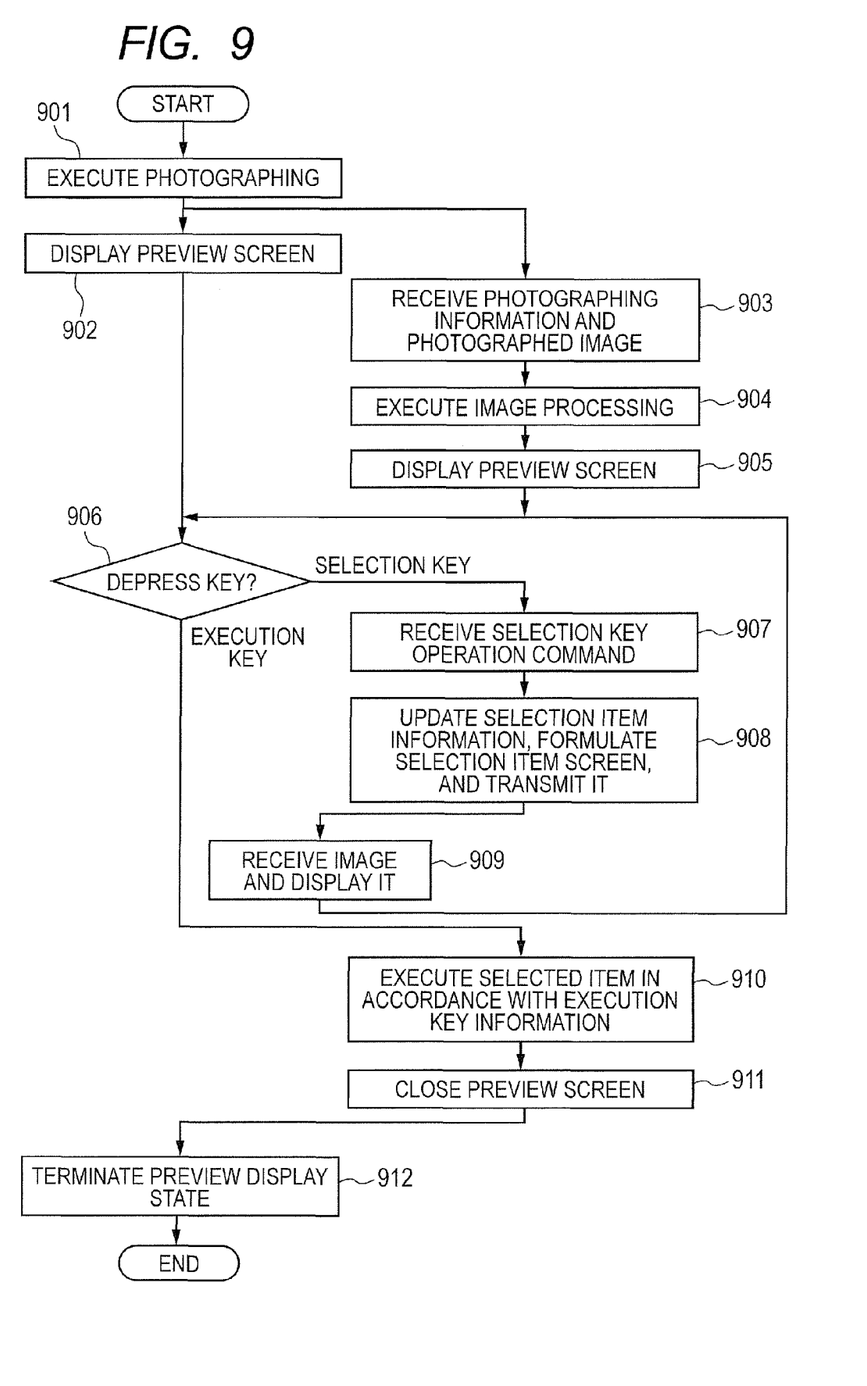
FIG. 9 is an example of a flowchart showing the preview operation of the ophthalmologic information process system.

FIG. 9 is a flowchart showing preview operation in the second embodiment. Before starting the operation, the system transmits an initial image to be displayed on the preview screen and causes the fundus camera to store the image.

In step 901, the operator depresses the photograph switch to photograph a fundus image. In step 902, the system displays a preview image of a photographed image on the fundus camera side. FIG. 7A shows an example of the preview image.

The application side receives photographing information and a photographed image immediately after the photographing processing in step 901 (step 903).

In step 904, the system performs an image process by using parameter information for an image process set by the photographed image acquired on the application side.

In step 905, the system displays, as a preview image, the image having undergone an image process upon completion of the image process on the application side. FIG. 7B shows an example of a preview image.

In step 906, the operator selects by operation on the fundus camera side whether to re-photograph the preview image by using the left and right keys as internal fixation target keys. When the operator performs selection key operation, the system receives selection key operation command information in step 907. In step 908, the system updates selection item information. The system generates a selection image of a preview screen by using updated information of selection items and transmits the generated image to the fundus camera.

In step 909, upon receiving an image on the fundus camera side, the camera displays the received image.

In step 906, when the operator selects the execution key, the fundus camera transmits operation information of the execution key to the application. In step 910, when the application receives the execution key, the application performing execution processing by using selection information. When the operator selects "OR", the system generates an image on the fundus camera at the time of observation and transmits the image to the fundus camera in step 911. In step 911, the system further executes "memory" on the preview screen on the application. Upon executing "memory", the system stores the photographed image and closes the preview screen.

When the operator selects "re-photograph", the system generates an image at the time of observation for the fundus camera and transmits the image to the fundus camera in step 911. In step 911, the system executes "delete" on the preview screen on the application. Upon executing "delete", the system deletes the photographed image.

In step 912, upon receiving the image, the fundus camera terminates the preview image and returns to the initial observation image to terminate the processing.

As described in the second embodiment, it is possible to synchronously execute processing on the application side and processing on the fundus camera side by only operation on the fundus camera side. This makes it possible to perform comfortable operation without performing any operation on the application side.

Third Embodiment

The third embodiment will exemplify a case in which an application is upgraded.

The following is an example of adding a new function as a selection item on the menu screen shown in the first embodiment when the application is upgraded and the new function is added.

Figure 10:
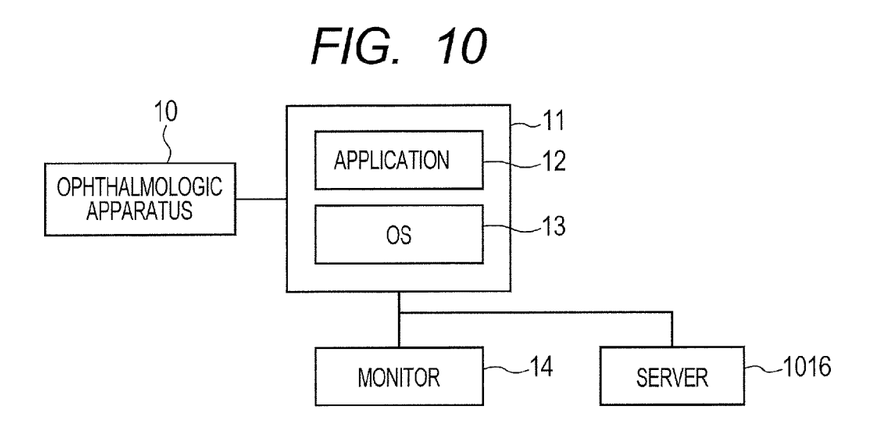
FIG. 10 is a view showing a connection example including the server of the ophthalmologic information process system.

Note that a file necessary for upgrading may be downloaded by connecting to a server 1016 via a communication line like a LAN, as shown in FIG. 10.

The third embodiment will exemplify a case in which "ON/OFF" for an image process at photographing is added to the application, and the function is selected on the menu screen. An image process at photographing includes, for example, a photographed, image process on the application, a process for changing the contrast, a blood vessel emphasizing process, and a process which can be used for diagnosis such as a papillary extraction process.

Upgrading changes a control portion 115, display manage portion 111, and display image 117 of an application 12.

The control portion 115 additionally includes processes to be performed when the image process at photographing is ON and OFF, respectively. The display manage portion 111 additionally includes "ON/OFF" of the process at photographing as selectable menu items. When the operator selects each item, the system adds a process of notifying the selected process to the control portion 115. The display image 117 additionally includes an image of "ON/OFF" of the process at photographing as a menu image.

Figure 11:
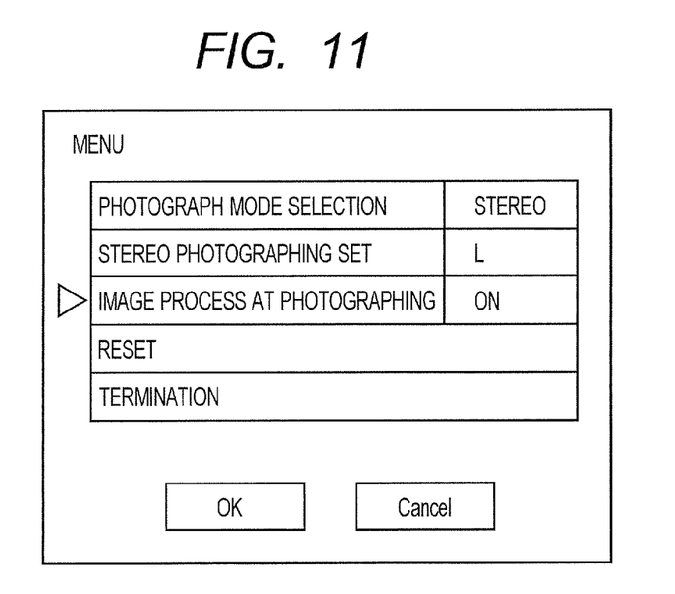
FIG. 11 is a view showing an example of a menu screen after upgrading of the ophthalmologic application.

FIG. 11 shows an example of a menu image after upgrading. Obviously, a function is added to FIG. 5A before upgrading.

As described in the third embodiment, when a change occurs on the application side due to upgrading, it is possible to add and select a menu item for function execution on the application side with respect to the menu screen by operation on the fundus camera side.

Applying this function will facilitate adding a menu item in a multilingual manner by replacing the display image 117 with a new display image with a change due to upgrading on the application side. Since the application side manages images for menus, it is possible to reduce the memory area on the ophthalmologic apparatus side.

Fourth Embodiment

Figure 12:
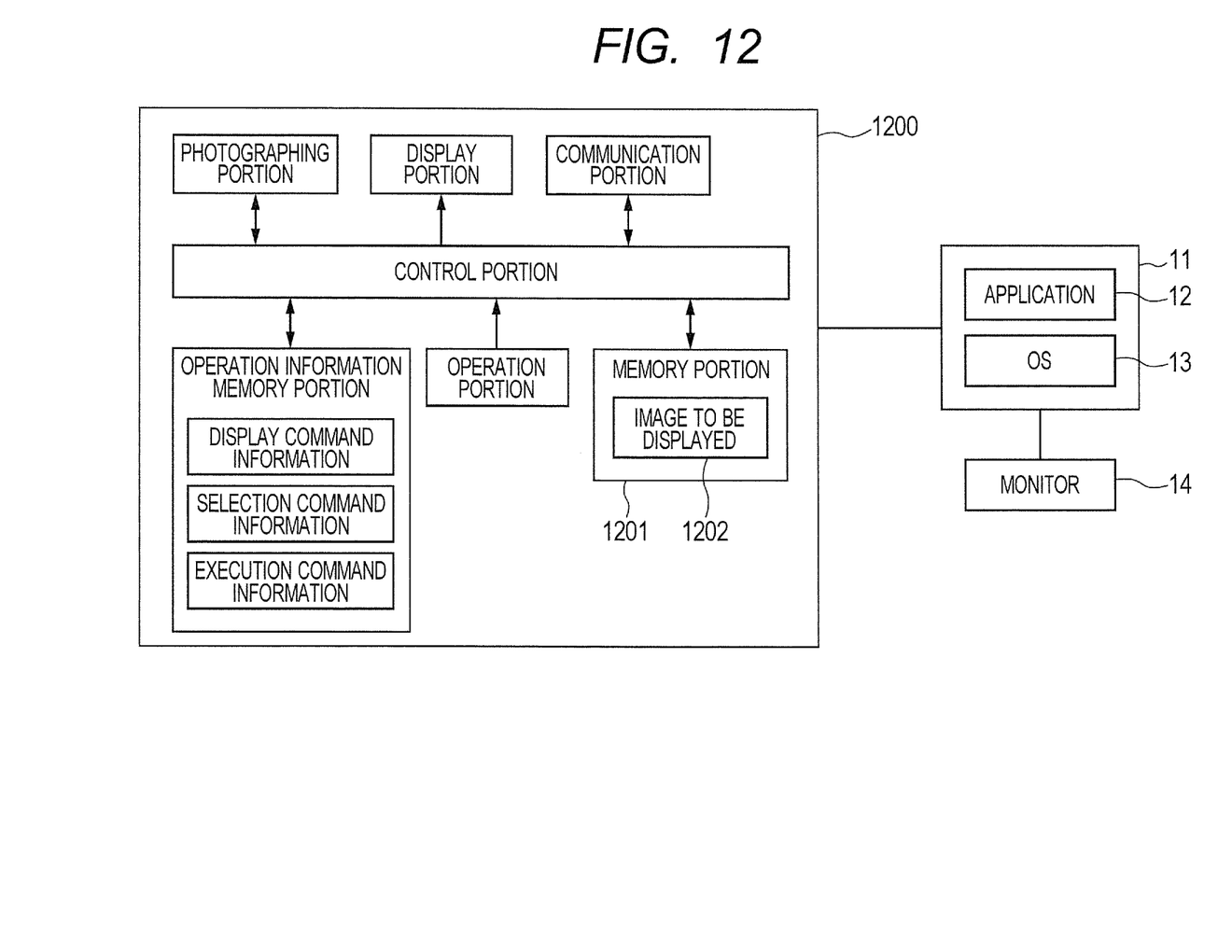
FIG. 12 is a block diagram showing an example of an arrangement in which the ophthalmologic apparatus includes a menu display function.

The fourth embodiment exemplifies an arrangement configured to make an ophthalmologic apparatus 1200 independently operate by mounting a memory portion 1201 and a display image 1202 in the ophthalmologic apparatus 1200 unlike the arrangement of the first embodiment.

In this arrangement, the ophthalmologic apparatus can operate singly under normal conditions. Connecting an application 12 to the ophthalmologic apparatus 1200 will generate a display image of menu items on the application side at the time of connection to the application and display, as selection items, "examination termination" and the like which can be executed by operation on the application. When the ophthalmologic apparatus operates singly without connection to any application, it is possible to display only items which can be executed by the ophthalmologic apparatus.

As described in the fourth embodiment, changing the display screen at the time of connection, to an application can make the application have a screen desired by the operator, thereby improving operability. In addition, when an ophthalmologic apparatus is replaced with a new one, the operator sometimes experiences a feeling of strangeness against a changed screen. In such a case, displaying the previous screen of the previously used ophthalmologic apparatus can return to familiar operation or set an arrangement according to the preference of the operator.

Other Embodiments

The present invention is also implemented by executing the following processing. That is, this is the processing of supplying software (programs) for implementing the functions of the above embodiments to a system or apparatus via a network or various types of storage media and making the computer (or the CPU, MPU, or the like) of the system or apparatus read out and execute the software.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-247027, filed Nov. 9, 2012, which is hereby incorporated by reference herein in its entirety.

What is claimed is:

1. An ophthalmologic system comprising:
   an ophthalmologic apparatus including a display unit configured to display a selection information image including a plurality of selectable items; and
   a computer connected to the ophthalmologic apparatus, wherein the ophthalmologic apparatus includes (1) a photographing unit configured to photograph an ophthalmologic image, and (2) an operation unit including a selection key that selects one item from the plurality of selectable items and an execution key that causes the computer to execute the selected item, and
   wherein the computer includes:
   (a) a reception unit configured to receive information including operation information of the operation unit which is transmitted from the ophthalmologic apparatus;
   (b) an image generation unit configured to generate the selection information image in which the selected item is emphasized in response to receiving the operation information indicating use of the selection key; and
   (c) a transmission unit configured to transmit the selection information image generated by the image generation unit to the ophthalmologic apparatus, and
   (d) a behavior control unit configured to control a behavior of the computer in response to receiving the operation information indicating use of the execution key.

2. A system according to claim 1, wherein the execution key functions as a selection information display key that causes the display unit to display selection information,
   wherein the computer further comprises a display manage unit configured to manage a selected state of the plurality of selectable items, and
   wherein the behavior control unit (a) causes the transmission unit to transmit the selection information image to the ophthalmologic apparatus so that the display unit displays the selection information image in response to receiving the operation information indicating use of the selection information display key, (b) causes the display manage unit to update the selected state of the plurality of selectable items in response to receiving the operation information indicating use of the selection key, (c) causes the image generation unit to generate the selection information image corresponding to the updated selected state in response to receiving the operation information indicating use of the selection key, and causes the transmission unit to transmit the selection information image to the ophthalmologic apparatus so that the display unit displays the selection information image, and (d) controls the behavior of the computer with the selected state in response to receiving the operation information indicating use of the execution key.

3. A system according to claim 1, wherein the execution key functions as a selection information display key that causes the display unit to display selection information,
   wherein the computer further comprises a display manage unit configured to manage a selected state of the plurality of selectable items, and
   wherein the behavior control unit (a) causes the transmission unit to transmit the selection information image to the ophthalmologic apparatus so that the display unit displays the selection information image in response to photographing the ophthalmologic image by the ophthalmologic apparatus, (b) causes the display manage unit to update a selected state of the selectable item in response to receiving the operation information indicating use of the selection key, (c) causes the image generation unit to generate a selection information image corresponding to the updated selected state in response to receiving the operation information indicating use of the selection key, and causes the transmission unit to transmit the selection information image to the ophthalmologic apparatus so that the display unit displays the selection information image, and (d) controls the behavior of the computer with the selected item in response to receiving the operation information indicating use of the execution key.

4. A system according to claim 1, wherein the ophthalmologic apparatus includes a key configured to operate a turn-on position of an internal fixation target which prompts visual fixation of an eye to be inspected and a key configured to highlight the internal fixation target, and wherein the selection key is assigned as a key configured to operate a turn-on position of the internal fixation target, and the execution key is assigned as a key configured to highlight the internal fixation target.

5. A system according to claim 1, wherein the plurality of selectable items includes an item representing examination termination with respect to an eye to be inspected.

6. A system according to claim 1, wherein when the execution key is operated while the selection information image is displayed on the display unit, display of the selection information image on the display unit is terminated, and initial display is restored.

7. A system according to claim 1, wherein the ophthalmologic apparatus (a) further includes a left/right eye detection unit configured to detect whether the eye to be inspected is a left or right eye and a left/right switching detection unit configured to detect that the left and right eyes to be inspected and photographed have been switched, and (b) terminates display of the selection information image on the display unit and restores initial display when the left/right switching detection unit detects that the left and right eyes to be inspected have been switched while the selection information image is displayed on the display unit.

8. A system according to claim 1, wherein the execution key functions as a selection information display key that causes the display unit to display selection information, wherein the ophthalmologic apparatus includes a photographing inhibition unit configured to inhibit the photographing, and wherein the photographing inhibition unit inhibits the photographing when the selection information display key is operated and the selection information image is displayed on the display unit.

9. A computer that is connected to an ophthalmologic apparatus including (1) a photographing unit configured to photograph an ophthalmologic image, (2) an operation unit including (a) a selection key which selects one item from a plurality of selectable items, and (b) an execution key which causes the computer to execute the selected item, and (3) a display unit configured to display a selection information image, the computer comprising:

a memory configured to store the plurality of selectable items;

a reception unit configured to receive information including operation information of the operation unit that is transmitted from the ophthalmologic apparatus;

an image generation unit configured to generate the selection information image including the plurality of selectable items and in which the selected item is emphasized in response to receiving the operation information indicating use of the selection key;

a transmission unit configured to transmit the selection information image generated by the image generation unit to the ophthalmologic apparatus so that the display unit displays the selection information image; and a behavior control unit configured to control a behavior of the computer in response to receiving the operation information indicating use of the execution key.

10. A computer according to claim 9, further comprising a display manage unit configured to manage a selected state of the plurality of selectable items, wherein the execution key functions as a selection information display key that causes the display unit to display selection information, and wherein the behavior control unit (a) causes the transmission unit to transmit the selection information image to the ophthalmologic apparatus so that the display unit displays the selection information image in response to receiving the operation information indicating use of the selection information display key, (b) causes the display manage unit to update the selected state of the plurality of selectable items in response to receiving the operation information indicating use of the selection key, (c) causes the image generation unit to generate the selection information image corresponding to the updated selected state in response to receiving the operation information indicating use of the selection key, and causes the transmission unit to transmit the selection information image to the ophthalmologic apparatus so that the display unit displays the selection information image, and (d) controls the behavior of the computer with the selected state in response to receiving the operation information indicating use of the execution key.

11. A computer according to claim 10, wherein the plurality of selectable items includes an item representing examination termination with respect to an eye to be inspected.

12. A computer according to claim 10, wherein when the execution key is operated while the selection information image is displayed on the display unit, display of the selection information image on the display unit is terminated, and initial display is restored.

13. A computer according to claim 9, further comprising a display manage unit configured to manage a selected state of the plurality of selectable items, wherein the execution key functions as a selection information display key that causes the display unit to display selection information, and wherein the behavior control unit (a) causes the transmission unit to transmit the selection information image to the ophthalmologic apparatus so that the display unit displays the selection information image in response to photographing the ophthalmologic image by the ophthalmologic apparatus, (b) causes the display manage unit to update a selected state of the selectable item in response to receiving the operation information indicating use of the selection key, (c) causes the image generation unit to generate a selection information image corresponding to the updated selected state in response to receiving the operation information indicating use of the selection key, and causes the transmission unit to transmit the selection information image to the ophthalmologic apparatus so that the display unit displays the selection information image, and (d) controls the behavior of the computer with the selected item in response to receiving the operation information indicating use of the execution key.

14. An ophthalmologic system comprising:

an ophthalmologic apparatus including (1) a photographing portion configured to photograph an ophthalmologic image, (2) a display unit configured to display an image including a plurality of selectable items, and (3) an operation unit including a selection key that selects one item from the plurality of selectable items; and a computer connected to the ophthalmologic apparatus, the computer including:

(a) a reception unit configured to receive information including operation information of the operation unit which is transmitted from the ophthalmologic apparatus;

(b) an image generation unit configured to generate the image in which the selected item is emphasized in response to receiving the operation information indicating use of the selection key; and (c) a transmission unit configured to transmit to the ophthalmologic apparatus, based on the operation information received by the reception unit, the image that was generated by the image generation unit.

15. A system comprising:

an ophthalmologic apparatus including (1) a photographing portion configured to photograph an ophthalmologic image, (2) a display unit configured to display an image including a plurality of selectable items; and (3) an operation unit including a selection key that selects one item from the plurality of selectable items and an execution key; and a computer connected to the ophthalmologic apparatus and caused to execute the selected item by the execution key, the computer including:

(a) a reception unit configured to receive information including operation information of the operation unit which is transmitted from the ophthalmologic apparatus; and (b) a behavior control unit configured to control a behavior of the computer in response to receiving the operation information indicating use of the execution key.

* * * * *